US011638839B2

(12) United States Patent
Zhu et al.

(10) Patent No.: US 11,638,839 B2
(45) Date of Patent: May 2, 2023

(54) DEVICE AND METHOD FOR MEASUREMENT OF PROTON BEAM SOURCE POSITION AND BEAMLINE CENTER POINT

(71) Applicant: Peking University, Beijing (CN)

(72) Inventors: Jungao Zhu, Beijing (CN); Xueqing Yan, Beijing (CN); Chen Lin, Beijing (CN)

(73) Assignee: Peking University, Beijing (CN)

( * ) Notice: Subject to any disclaimer, the term of this patent is extended or adjusted under 35 U.S.C. 154(b) by 0 days.

(21) Appl. No.: 17/088,714

(22) Filed: Nov. 4, 2020

(65) Prior Publication Data
US 2021/0302600 A1     Sep. 30, 2021

(30) Foreign Application Priority Data

Mar. 30, 2020  (CN) .......................... 202010236443.6

(51) Int. Cl.
*A61N 5/10*     (2006.01)
*G01T 1/29*     (2006.01)
(Continued)

(52) U.S. Cl.
CPC ......... *A61N 5/1078* (2013.01); *A61N 5/1077* (2013.01); *G01T 1/2914* (2013.01);
(Continued)

(58) Field of Classification Search
CPC ............... A61N 5/1077; A61N 5/1078; A61N 2005/1087; A61N 2005/1088; G01T 1/29; G01T 1/2914; G21K 5/04
(Continued)

(56) References Cited

U.S. PATENT DOCUMENTS 5,760,395 A  *  6/1998  Johnstone ................ A61N 5/10
                                                        850/62
7,432,516 B2 * 10/2008  Peggs .................... H05H 13/04
                                                        315/501
(Continued)

OTHER PUBLICATIONS

Fernado Brandi et al., A Few MeV Laser-Plasma Accelerated Proton Beam in Air Collimated Using Compact Permanent Quadrupole Magnets, Appl. Sci. 11, 6358 (2021). (Year: 2021).*
(Continued)

*Primary Examiner* — Allen C. Ho
(74) *Attorney, Agent, or Firm* — Neugeboren O'Dowd PC

(57) ABSTRACT

A device and a method for measuring proton beam source position and beamline center are disclosed. The device includes N quadrupole magnets, a laser, a target and a scintillation screen; the target and the scintillation screen are arranged in front of and behind the N-quadrupole lens, respectively; the N-quadrupole lens can be converted to a M-quadrupole lens; the position of proton beam after being focused by the N- or M-quadrupole lens on the scintillation screen is measured; according to the amplification factor and the proton beam position, the offset of the proton beam source from the beamline center, as well as the position of the beamline center on the scintillation screen are calculated; the disclosure can accurately determine the position of the beamline center and the proton beam source by the use of N quadrupole magnets, combined with a scintillation screen.

3 Claims, 1 Drawing Sheet

(51) Int. Cl.
*G21K 5/04* (2006.01)
*G21G 1/10* (2006.01)

(52) U.S. Cl.
CPC .............. *G21G 1/10* (2013.01); *G21K 5/04* (2013.01); *A61N 2005/1087* (2013.01); *A61N 2005/1088* (2013.01)

(58) Field of Classification Search
USPC ................. 250/396 R, 396 ML, 423 R, 424
See application file for complete search history.

(56) References Cited

U.S. PATENT DOCUMENTS

| | | | | |
|---|---|---|---|---|
| 8,530,852 | B2* | 9/2013 | Le Galloudec | H01J 1/13 250/423 P |
| 9,937,360 | B1* | 4/2018 | Papeer | A61N 5/1081 |
| 10,039,935 | B1* | 8/2018 | Papeer | A61N 5/1081 |
| 10,395,881 | B2* | 8/2019 | Papeer | G21K 5/04 |
| 10,413,755 | B1* | 9/2019 | Sahadevan | A61N 5/1042 |
| 10,705,036 | B2* | 7/2020 | Antici | G01N 23/2257 |
| 10,714,225 | B2* | 7/2020 | Ylimaki | G21G 1/10 |
| 10,847,340 | B2* | 11/2020 | Papeer | G21K 1/093 |

OTHER PUBLICATIONS

Y. X. Geng, D. Wu, and W. Yu et al., Proton beams from intense laser-solid interaction: Effects of the target materials, Matter and Radiation at Extremes 5, 064402 (2020). (Year: 2020).*
C. McGuffey, J. Kim, and M. S. Wei et al., Focusing Protons from a Kilojoule Laser for Intense Beam Heating using Proximal Target Structures. Scientific Reports 10, 9415 (2020). (Year: 2020).*
J. G. Zhu et al., Experimental demonstration of a laser proton accelerator with accurate beam control through image-relaying transport, Physical Review Accelerators and Beams 22, 061302 (2019). (Year: 2019).*
J. S. Green, A. P. L. Robinson, and N. Booth et al., High efficiency proton beam generation through target thickness control in femtosecond laser-plasma interactions, Appl. Phys. Lett. 104, 214101 (2014). (Year: 2014).*
M. Nishiuchi, I. Daito, and M. Ikegami et al., Focusing and spectral enhancement of a repetition-rated, laser-driven, divergent multi-MeV proton beam using permanent quadrupole magnets, Appl. Phys. Lett. 94, 061107 (2009). (Year: 2009).*
J. Polz et al., Efficient Laser-Driven Proton Acceleration from a Cryogenic Solid Hydrogen Target. Scientific Reports 9, 16534 (2019). (Year: 2019).*

* cited by examiner

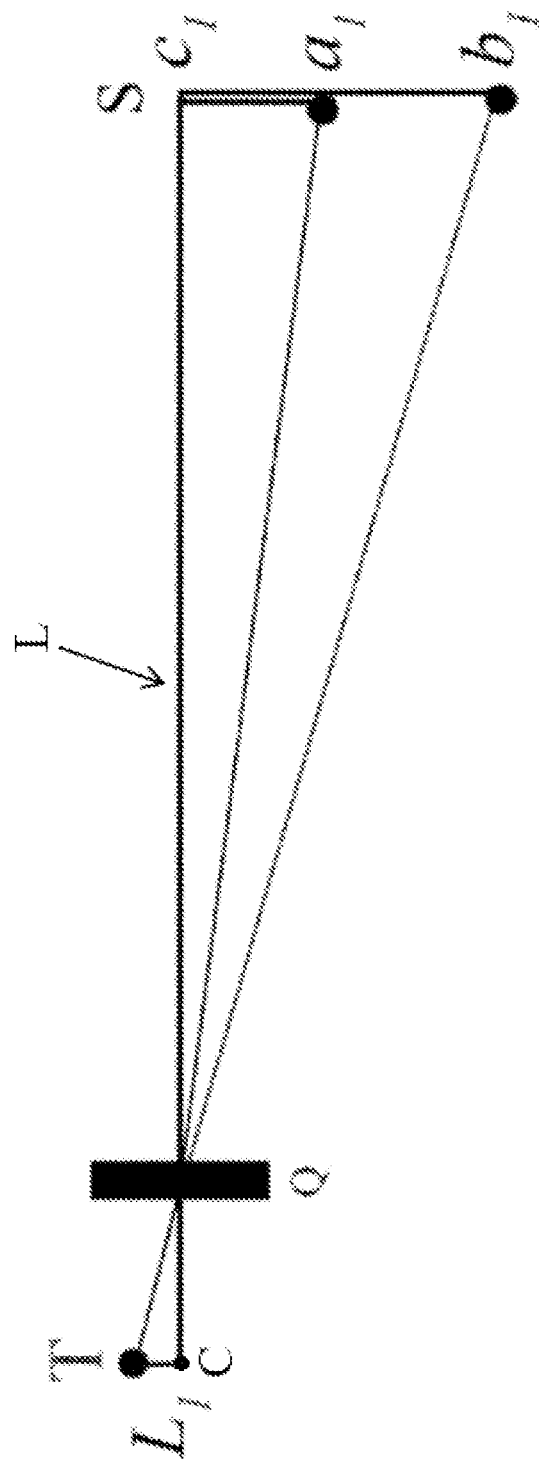

DEVICE AND METHOD FOR MEASUREMENT OF PROTON BEAM SOURCE POSITION AND BEAMLINE CENTER POINT

CLAIM OF PRIORITY UNDER 35 U.S.C. § 119

This application claims the priority of Chinese Patent Application No. 202010236443.6, entitled "Device and method for measurement of proton beam source position and beamline center" filed with the China National Intellectual Property Administration on Mar. 30, 2020, which is incorporated herein by reference in its entirety.

TECHNICAL FIELD

The disclosure relates to application technology for beam centering in a laser accelerator, in particular to a device and a method for measuring the proton beam source position and the beamline center point.

BACKGROUND

Accelerators play increasingly important roles in human scientific research and life. Besides leading-edge scientific research such as large-scale colliders, accelerators play an irreplaceable role in the field of cancer treatment. Traditional treatment of tumors by photons inevitably causes damage to shallow healthy tissues. Protons and heavy ions produced by accelerators significantly improve the damage to shallow healthy tissues, which benefits from the more concentrated end energy deposition of the Bragg peak. Therefore, therapy with protons or heavy ions has huge advantages. However, conventional radio-frequency accelerators are large in size, high in cost, and expensive in maintenance and operation, which limits the wide application of therapy with protons or heavy ions.

When a high-intensity laser pulse interacts with a target, the acceleration gradient can reach more than 100 GV/m (3 orders of magnitude higher than that of a radio-frequency accelerator), which is not limited by electrical breakdown, and can significantly reduce the size and cost of the accelerator. Proton beams with energy close to 100 MeV have been reported in a laser accelerator. The laser accelerator is gradually becoming mature, and has attracted more and more attention in many fields.

After the high-intensity laser interacts with the target, proton beams are generated. The proton beam usually needs focusing and energy selection with a beamline before application. It is required that the proton beam is positioned accurately in the center of the beamline to ensure accurate transmission. Misalignment of the proton beam source could cause inaccurate energy selection and deviation of beam spot position at the irradiation point during cancer treatment. The usual centering method is to determine the proton beam source position where the laser interacts with the target and the central axis of the focusing element such as a quadrupole triplet lens using a simulating light. This method is troublesome and inaccurate, as has been proven in experiments.

SUMMARY

In view of the above existing problems in the prior art, the present disclosure proposes a device and a method for measuring the proton beam source position and the beamline center point, with which the position of the beamline center point and the displacement of the proton beam source from the central axis of the beamline can be determined easily and accurately.

An object of the present disclosure is to provide a device for measuring the position of the proton beam source and the beamline center point.

According to the present disclosure, the device for measuring the proton beam source position and the beamline center point includes: N quadrupole magnets, a laser, a target and a scintillation screen, wherein N quadrupole magnets are coaxially arranged in a straight line along the central axis of the beamline to form an N-quadrupole lens; there is a distance between adjacent quadrupole magnets; N is a natural number≥3;

the target that interacts with the high-intensity laser to generate a proton beam is arranged in front of the N-quadrupole lens on the central axis of the beamline;

the scintillation screen is arranged behind the N-quadrupole lens, and the detection plane of the scintillation screen is perpendicular to the central axis of the beamline;

a high-intensity laser pulse is generated by the laser, and interacts with the target to generate a proton beam, which is transmitted along the central axis of the beamline;

after being focused by the N-quadrupole lens, the beam spot position measured on the scintillation screen is $a_1$ in the horizontal direction, and $a_2$ in the vertical direction, and the amplification factor after being focused by the N-quadrupole lens onto the scintillation screen is $F_1$ in the horizontal direction, and $F_3$ in the vertical direction;

the N-quadrupole lens is converted to M-quadrupole lens made of M quadrupole magnets, wherein M<N and M is a natural number≥2;

a high-intensity laser pulse is generated by the laser, and interacts with the target to generate a proton beam, which is transmitted along the central axis of the beamline;

after being focused by the M-quadrupole lens, the beam spot position measured on the scintillation screen is $b_1$ in the horizontal direction, and $b_2$ in the vertical direction, and the amplification factor after being focused by the M-quadrupole lens onto the scintillation screen is $F_2$ in the horizontal direction, and $F_4$ in the vertical direction;

according to the amplification factor and the beam spot position, the offsets $L_1$ and $L_2$ of the proton beam source from the central axis of the beamline in the horizontal and vertical directions respectively, as well as the beamline center point positions $c_1$ and $c_2$ in the horizontal and vertical directions respectively on the scintillation screen are calculated respectively:

$$L_1 = \frac{a_1 - c_1}{F_1} = \frac{b_1 - c_1}{F_2}$$

$$L_2 = \frac{a_2 - c_2}{F_3} = \frac{b_2 - c_2}{F_4}.$$

With the optimization of the distance between adjacent quadrupole magnets, it can be achieved that the proton beam has high transmission efficiency and the quadrupole magnet has suitable magnetic field strength. In the present disclosure, the distance between adjacent quadrupole magnets is between 6 and 10 cm. Keeping a distance greater than 6 cm can meet the requirements of mechanical design while reducing the required magnetic field strength; keeping a distance less than 10 cm can realize focusing in a compact space, which can avoid excessively large proton beam envelopes in the horizontal and vertical directions and the reduction of transmission efficiency. The distance is determined by the comprehensive requirements of focusing and transmission efficiency. If the distance is too small, a higher magnetic field strength is required; if the distance is too large, the beam envelope is larger and the transmission efficiency is reduced.

The magnetic field strength of the quadrupole magnet is determined by the beamline layout and the beam energy. For example, when a 5 MeV proton beam is focused, the magnetic field strength usually does not exceed 0.26 T/cm. The magnetic field strength of the quadrupole magnet can be adjusted by the current.

Then, the N-quadrupole lens is converted to the M-quadrupole lens by turning off (N–M) quadrupole magnets in the N-quadrupole lens.

The amplification factors of the proton beam after being focused by the N-quadrupole lens and the M-quadrupole lens onto the scintillation screen are determined by the beamline layout, and can be obtained by theoretical calculations.

Another object of the present disclosure is to provide a method for measuring the proton beam source position and beamline center point.

The method for measuring the proton beam source position and beamline center point of the present disclosure includes the following steps:

1) arranging N quadrupole magnets coaxially in a straight line along the central axis of the beamline to form a N-quadrupole lens; there is a distance between adjacent quadrupole magnets, and N is a natural number≥3;

arranging a target and a scintillation screen respectively at the two ends of the N-quadrupole lens, and making the detection plane of the scintillation screen be perpendicular to the central axis of the beamline;

2) generating a high-intensity laser pulse by the laser, and the laser pulse interacting with the target to generate a proton beam, which is transmitted along the central axis of the beamline;

after being focused by the N-quadrupole lens, the position of the beam spot measured on the scintillation screen is a1 in the horizontal direction, and a2 in the vertical direction, and the amplification factor of the proton beam after being focused by N-quadrupole lens onto the scintillation screen is F1 in the horizontal direction, and F3 in the vertical direction;

3) converting the N-quadrupole lens to M-quadrupole lens, wherein M<N and M is a natural number≥2;

4) generating a high-intensity laser pulse by the laser, and the laser pulse interacting with the target to generate a proton beam, which is transmitted along the central axis of the beamline;

after being focused by the M-quadrupole lens, the position of the beam spot measured on the scintillation screen is $b_1$ in the horizontal direction, and $b_2$ in the vertical direction, and the amplification factor of the proton beam after being focused by M-quadrupole lens onto the scintillation screen is $F_2$ in the horizontal direction, and $F_4$ in the vertical direction; and 5) calculating the offsets $L_1$ and $L_2$ of the proton beam source from the central axis of the beamline in the horizontal and vertical directions respectively, as well as the beamline center point positions $c_1$ and $c_2$ in the horizontal and vertical directions respectively on the scintillation screen respectively according to the amplification factor and the beam spot position:

$$L_1 = \frac{a_1 - c_1}{F_1} = \frac{b_1 - c_1}{F_2}$$

$$L_2 = \frac{a_2 - c_2}{F_3} = \frac{b_2 - c_2}{F_4}.$$

Advantages of the disclosure are as follows:

The disclosure can accurately determine the beamline center position and the proton beam source by the use of N-quadrupole lens and M-quadrupole lens which is converted from the N-quadrupole lens, a scintillation screen and the difference in amplification factors, thereby achieving high-precision centering.

BRIEF DESCRIPTION OF THE DRAWINGS

FIG. 1 is a schematic diagram of an example device for measuring the proton beam source position and beamline center point in the horizontal direction of the present disclosure.

DETAILED DESCRIPTION

The present disclosure will be further explained below through specific embodiments with reference to the drawings.

Theoretically, it is required that the proton beam source generated by the interaction of the laser pulse and the target, the N-quadrupole lens and the scintillation screen are all located on the central axis of the beamline. In experiment, this is usually performed by simulating light. While there are deviations and difficulties in practical operation to achieve the centering accuracy of the order of microns. In experiment, the target needs to be disassembled and replaced frequently, and the laser needs to be adjusted frequently. Therefore, when the target is replaced and the experiment is restarted each time, the proton beam source position generated by the laser pulse and the target will vary. In the experiment, due to the limitations of the target position control system and possible errors, such as system crash, the proton beam source position will change. The method according to the disclosure can be used to determine and correct the offset of proton beam source position in time. It is difficult to accurately determine the beamline center point on the scintillation screen; in addition, the scintillation screen needs to be moved when the proton beam is not detected, thus it needs to be moved frequently. The method according to the present disclosure can accurately and conveniently determine the position of the beamline center point on the scintillation screen.

The device for measuring a position of a proton beam source and a beamline center point C is seen in FIG. 1. Element L in FIG. 1, which extends from element C in FIG. 1 to element $c_1$ in FIG. 1 comprises a central axis of the beamline. Element C in FIG. 1 comprises the beamline center point C. The device for measuring a position of a proton beam source and a beamline center point C includes: a quadrupole triplet lens Q, a laser, a target T and a scintillation screen S, wherein three quadrupole magnets are coaxially arranged in a straight line along the the central axis of the beamline L to form the quadrupole triplet lens Q and there is a distance between adjacent quadrupole magnets. Target T is arranged in front of the quadrupole triplet lens Q and the scintillation screen S is arranged at 165 cm behind the quadrupole triplet lens Q. A detection plane of the scintillation screen S is arranged perpendicularly to the central axis to the beamline L. A high-intensity laser pulse is generated by the laser, with the high intensity laser pulse: (a) interacting with the target T to generate a proton beam and (b) transmitted along the central axis of the beamline L. After the high intensity laser pulse is focused by the quadrupole triplet lens Q, the position of the proton beam on the scintillation screen S is $a_1$ in the horizontal direction and the amplification factor of the proton beam on the scintillation screen S is $F_1$ in the horizontal direction. The magnetic field strengths of the quadrupole magnets are 0.133, −0.111 and 0.134 T/cm respectively. The quadrupole triplet lens Q is converted to a quadrupole doublet lens by turning off the third quadrupole magnet. When the high-intensity laser pulse is generated by the laser after converting the quadrupole triplet lens Q to the quadrupole doublet lens and the high-intensity laser pulse interacts with the target T to generate a proton beam, the proton beam from the quadrupole doublet lens is also transmitted along the central axis of the beamline L. After being focused by the quadrupole doublet lens, the position of the proton beam from the quadrupole doublet lens on the scintillation screen S is $b_1$ in the horizontal direction and the amplification factor of the proton beam on the scintillation screen S is $F_2$ in the horizontal direction. The magnetic field strengths of the quadrupole magnets are 0.251 and −0.076 T/cm respectively.

In the embodiment, the amplification factor $F_1$ of the proton beam on the scintillation screen S after being focused by the quadrupole triplet lens is −2.488 in the horizontal direction, and the amplification factor $F_2$ of the proton beam on the scintillation screen S after being focused by the quadrupole doublet lens is −17.332 in the horizontal direction. The pixel value in the image measured in the experiment is: $a_1$=866, $b_1$=906. According to the amplification factor and the position of the proton beam, the offset of the proton beam source from the central axis of the beamline is calculated as follows:

$$L_1 = \frac{a_1 - c_1}{F_1} = \frac{b_1 - c_1}{F_2},$$

wherein $c_1$ is the position of the beamline center point on the scintillation screen in the horizontal direction, and $c_1$ is calculated as 859.3. According to the distance relationship between the pixel and the actual size, the offset $L_1$ of the proton beam source from the beamline center point is calculated as 0.128 mm in horizontal direction.

After moving the target by 0.13 mm, it is measured that $a_1$=861 and $b_1$=863, and it is calculated that $c_1$=860.7. According to the distance relationship between the pixel and the actual size, it can be obtained that $L_1$=0.006 mm. After adjustment, the deviation of the proton beam source from the central axis of the beamline in the horizontal direction is only 6 μm.

Using the same method, the offset of the proton beam source from the central axis of the beamline in the vertical direction can be measured and corrected.

Finally, it should be noted that the disclosure of the embodiments is to help further understand the present disclosure, and those skilled in the art can understand that various substitutions and modifications are possible without departing from the spirit and scope of the present disclosure and the appended claims. Therefore, the present disclosure should not be limited to the content disclosed in the embodiments, and the scope of protection of the present disclosure is defined by the claims.

What is claimed is:

1. A device for measuring a position of a proton beam source and a beamline center point, including:
   N quadrupole magnets,
   a laser,
   a target, and
   a scintillation screen,
   wherein:
      the N quadrupole magnets are coaxially arranged in a straight line along a central axis of a beamline to form an N-quadrupole lens;
      there is a distance between adjacent quadrupole magnets of the N quadrupole magnets;
      N is a natural number>3;
      the target interacts with a high-intensity laser pulse generated by the laser to generate a proton beam;
      the target is arranged in front of the N-quadrupole lens along the central axis of the beamline;
      the scintillation screen is arranged behind the N-quadrupole lens;
      a detection plane of the scintillation screen is perpendicular to the central axis of the beamline;
      the laser is configured to generate the high-intensity laser pulse, which interacts with the target to generate a proton beam;
      the proton beam is transmitted along a direction of the central axis of the beamline;
      after being focused by the N-quadrupole lens, a position of the proton beam measured on the scintillation screen is $a_1$ in a horizontal direction, and $a_2$ in a vertical direction, and an amplification factor of the proton beam after being focused by the N-quadrupole lens onto the scintillation screen is $F_1$ in the horizontal direction, and $F_3$ in the vertical direction.

2. The device for measuring the position of the proton beam source and the beamline center point according to claim 1, wherein the distance between adjacent quadrupole magnets is between 6 cm and 10 cm.

3. A method for measuring a position of a proton beam source and a beamline center point by using the device according to claim 1, including the following steps:
   1) arranging N quadrupole magnets coaxially in a straight line along a central axis of a beamline to form an N-quadrupole lens, wherein there is a distance between adjacent magnets of the N quadrupole magnets, and N is a natural number≥3;
   2) arranging a target and a scintillation screen respectively at two ends of the N-quadrupole lens, and making a detection plane of the scintillation screen to be perpendicular to the central axis of the beamline;
   3) generating a high-intensity laser pulse by a laser, and the high-intensity laser pulse interacting with the target to generate a proton beam, which is transmitted along a direction of the central axis of the beamline;
   4) after being focused by the N-quadrupole lens, a position of a beam spot of the proton beam measured on the scintillation screen is $a_1$ in a horizontal direction, and $a_2$ in a vertical direction, and an amplification factor of the proton beam after being focused by the N-quadrupole lens onto the scintillation screen is $F_1$ in the horizontal direction, and $F_3$ in the vertical direction;
   5) converting the N-quadrupole lens to an M-quadrupole lens, wherein M<N and M is a natural number≥2;

6) generating a high-intensity laser pulse by the laser, and the high-intensity laser pulse interacting with the target to generate a proton beam, which is transmitted along the direction of the central axis of the beamline;

7) after being focused by the M-quadrupole lens, a position of a beam spot of the proton beam measured on the scintillation screen is $b_1$ in the horizontal direction, and $b_2$ in the vertical direction, and an amplification factor of the proton beam after being focused by the M-quadrupole lens onto the scintillation screen is $F_2$ in the horizontal direction, and $F_4$ in the vertical direction; and 8) calculating offsets $L_1$ and $L_2$ of a proton beam source from the beamline center point in the horizontal direction and the vertical direction respectively, as well as positions $C_1$ and $C_2$ of the beamline center point in the horizontal direction and the vertical direction respectively on the scintillation screen according to the amplification factor of the proton beam after being focused by the N-quadrupole lens onto the scintillation screen and the amplification factor of the proton beam after being focused by the M-quadrupole lens onto the scintillation screen and the position of the beam spot of the proton beam after being focused by the N-quadrupole lens and the position of the beam spot of the proton beam after being focused by the M-quadrupole lens:

$$L_1 = \frac{a_1 - c_1}{F_1} = \frac{b_1 - c_1}{F_2}$$

$$L_2 = \frac{a_2 - c_2}{F_3} = \frac{b_2 - c_2}{F_4}.$$

* * * * *